US00PP08119P

United States Patent [19]

Stoots

[11] Patent Number: Plant 8,119

[45] Date of Patent: Jan. 26, 1993

[54] VARIETY OF GERANIUM NAMED SARAH

[75] Inventor: Eleanor Stoots, Connellsville, Pa.

[73] Assignee: Oglevee, Ltd., Connellsville, Pa.

[21] Appl. No.: 791,279

[22] Filed: Nov. 13, 1991

[51] Int. Cl.[5] ..... A01H 5/00
[52] U.S. Cl. ..... Plt./87.12
[58] Field of Search ..... Plt./87.12

*Primary Examiner*—James R. Feyrer

*Attorney, Agent, or Firm*—Webb, Burden, Ziesenheim & Webb

[57] ABSTRACT

The new cultivar is characterized by the rich rose pink colored bloom which is very slow to shatter and has strong tolerance to heat. The short internodes and low basal branching results in a variety that is both a good cutting producer and an excellent outdoor garden cultivar.

1 Drawing Sheet

BACKGROUND OF THE INVENTION

The present invention comprises a new and distinct cultivar of *Pelargonium* × *hortorum* known by the varietal name Sarah (Oglevee No. 8027). The new variety was discovered in a selected breeding program on Sep. 2, 1987 in Connellsville, Pa. The new variety is a selection from the crossing of Veronica (U.S. Plant Pat. No. 5,054) and Katie (U.S. Plant Pat. No. 5,759) carried out using embryo rescue techniques. Sarah is similar to Veronica with its compact habit, leaf shape and leaf coloration and outdoor performance. The bloom color of this new variety is different from both Veronica and Katie.

The new variety was first asexually reproduced by cuttings at Oglevee Ltd. in Connellsville, Pa. The new variety has been asexually reproduced by cuttings at Oglevee Ltd. in Connellsville, Pa. over a three-year period. It has also been trial and field tested at Connellsville and has been found to retain its distinctive characteristics through successive propagations.

The cultivar when grown in a glass greenhouse in Connellsville, Pa. using natural light and 60° F. night, 68° F. day and 71° F. vent, has a response time of six weeks from a rooted cutting to flowering in a 10 cm. pot. The response time was determined on plants grown in soilless media employing constant fertilizer of 200 parts per million of nitrogen and potassium in full light. The rooted cuttings were potted Feb. 14, 1990 and flowered on Apr. 1, 1990.

DESCRIPTION OF THE DRAWING

FIG. 1 of the accompanying photographic drawing illustrates the new cultivar the color being as nearly true as possible with color illustrations of this type.

DESCRIPTION OF THE NEW PLANT

The following detailed description sets forth the characteristics of the new cultivar. The data which defines these charcteristics were collected by asexual reproductions carried out by Oglevee Ltd. in Connellsville, Pa. The plant history was taken on six week plants blossomed under natural light in a greenhouse and the color readings were taken indoors under 150–175 foot candles of florescent cool white light. Color references are primarily to The R.H.S. Color Chart of The Royal Horticultural Society of London.

THE PLANT

Classification:
- *Botanical.*—*Pelargonium* × *hortorum.*
- *Commercial.*—Zonal Geranium.

Form: Upright habit; free basal branching, early flowering.
- *Height.*—16.0 to 18.0 cm. from media surface.
- *Growth.*—Compact mound shape, short internodes; prolific blooming.

Strength: Stands upright without artificial support; sturdy compact habit.

Foliage: Stalked leaf attachment; zoning present.

Leaves:
- *Size.*—7.0 to 8.5 cm. across.
- *Shape.*—Reniform; cordate base.
- *Margin.*—Crenate.
- *Texture.*—Pubescent; slightly reflective; leathery.
- *Color.*—Top: Green Group 137A. Zone: Yellow-Green Group 147A. Bottom: Yellow-Green Group 147B.
- *Ribs and veins.*—Palmate venation Color: Yellow-Green Group 147C.

Petioles:
- *Color.*—Yellow-Green Group 146B.
- *Length.*—6.0 to 10.0 cm.

Stem:
- *Color.*—Yellow-Green Group 146C.
- *Internodes.*—1.5 to 3.0 cm. in length.

THE BUD

Shape: Upright; hemispherical cluster.

Size: 2.5 to 3.5 cm. across.

INFLORESCENCE

Blooming habit: Continuous blooming; upright; semi-double; hemispherical; slow to shatter.

Size: 9.0 to 12.0 cm. across.

Borne: Umbel; 6.0 to 8.0 cm. above foliage; florets on pedicel, pedicel on peduncle.

Florets:
- *Form.*—Flat to slightly cupped.
- *Color.*—Top: Red Group 50B with a shading of Red Group 41C on the throat. Bottom: Red Group 48C.
- *Petals.*—Obovate; margin entire; smooth, flat to slightly cupped; separate, not united; 7–8 in number.

*Size.*—(Floret) 4.0 to 4.5 cm. across.

*Texture and appearance.*—Smooth; appearance from a distance is a rich rose pink bloom and deep green foliage.

Petaloids:

*Quantity.*—2–4 in number.

*Shape.*—Narrow, elongated, twisted, some petal-like.

*Color.*—Top: Red Group 50B. Bottom: Red Group 48C.

Pedicel:

*Length.*—3.0 to 3.5 cm.

*Color.*—Yellow-Green Group 146C.

Peduncle: Arises from node opposite leaf petiole.

*Length.*—12.5 to 16.0 cm.

*Color.*—Yellow-Green Group 146B.

Persistence: Non-shattering flower.

Lasting Quality: Bloom is very slow to shatter; heat tolerant.

REPRODUCTIVE ORGANS

Stamens:

*Anthers.*—2.0 mm. in length, 6–7 in number.

*Filaments.*—Irregular shape; flat.

*Color.*—White to pink at anther end.

*Length.*—6.0 to 8.0 mm.

*Pollen.*—Golden brown.

Pistils:

*Number.*—One.

*Length.*—7.0 to 8.0 mm.

*Stigma.*—5 parted; pinkish in color.

*Style.*—2.0 to 3.0 mm. in length.

Ovaries: Superior; yellow-green; pubescent.

Fruit: None observed.

GENERAL CHARACTERISTICS

This new variety is characterized by its compact plant habit and the rich rose pink bloom. Short internodes and low basal branching allows the plant to be both a good cutting producer and an excellent outdoor garden cultivar.

Sarah has gained the good traits from both its parents including the dark green foliage and compact plant habit of Veronica and Sarah actually has a richer color than Katie.

I claim:

1. A new and distinct variety of Geranium plant substantially as shown and described.

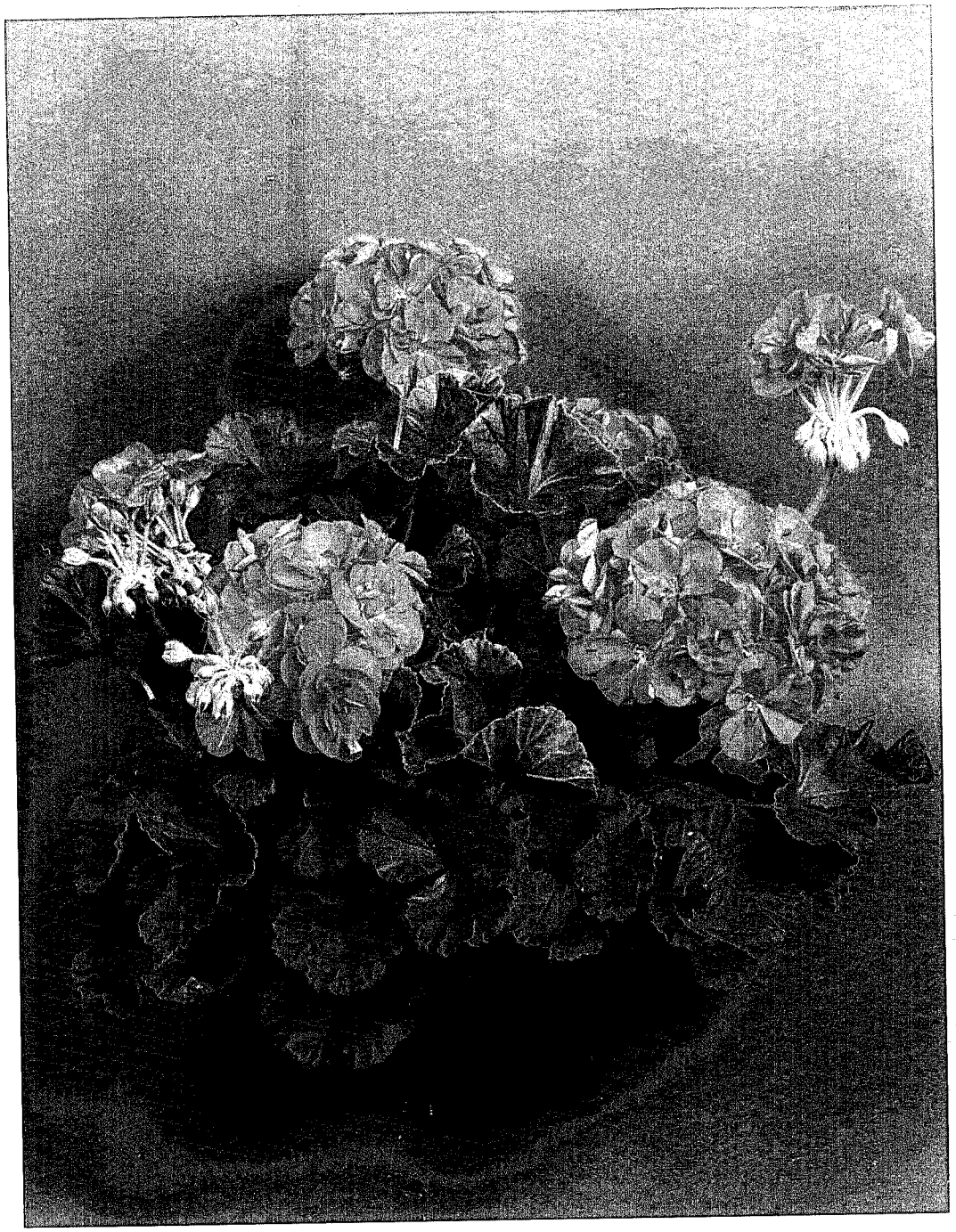

* * * * *